Figure 1:
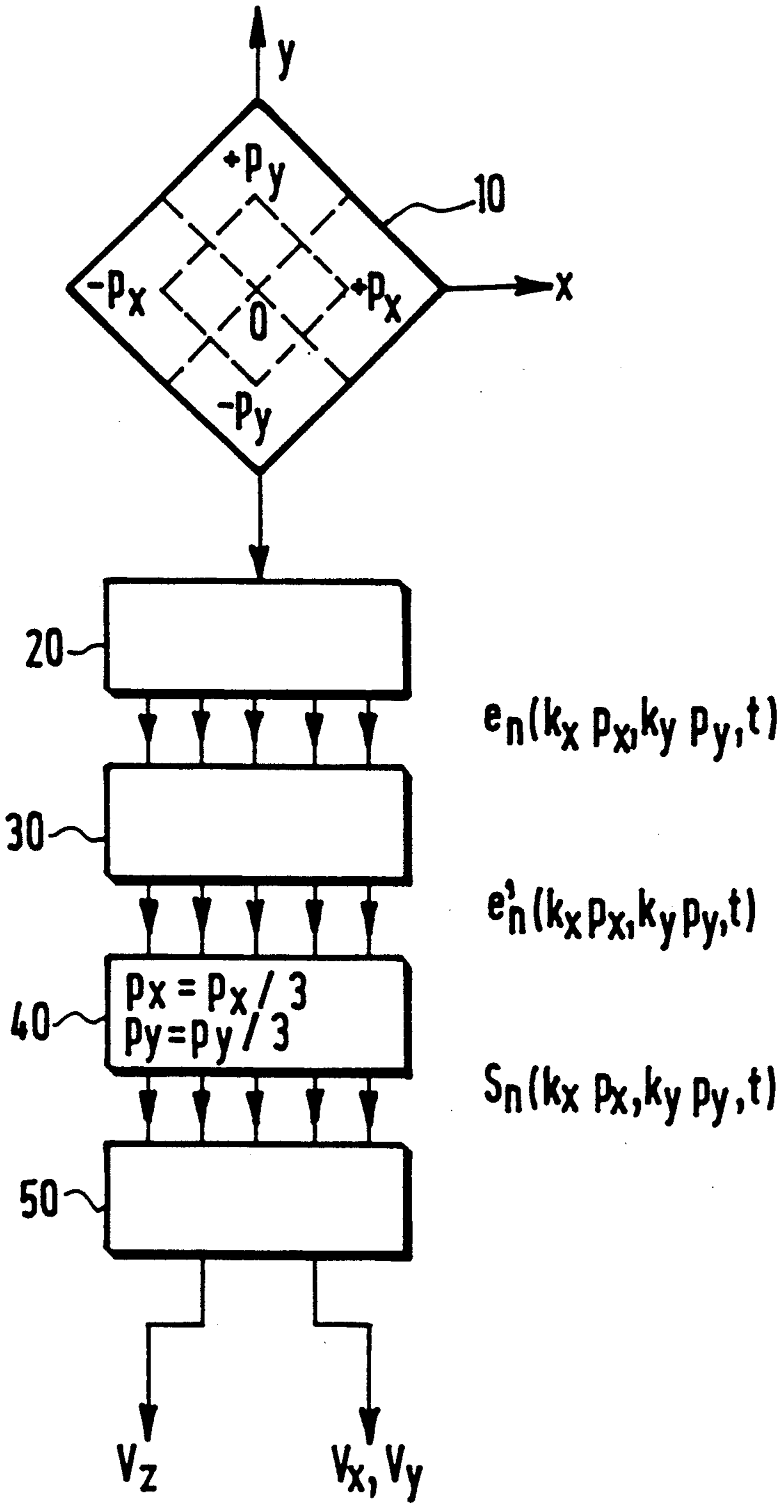

United States Patent [19]
Bonnefous

[11] Patent Number: 5,000,184
[45] Date of Patent: Mar. 19, 1991

[54] DIRECTIONAL COMPONENT MEASUREMENT BY ECHOGRAPHY

[75] Inventor: Odile Bonnefous, Nogent sur Marne, France

[73] Assignee: U.S. Philips Corporation, New York, N.Y.

[21] Appl. No.: 407,517

[22] Filed: Sep. 15, 1989

[30] Foreign Application Priority Data

Sep. 30, 1988 [FR] France ................................ 88 12806

[51] Int. Cl.[5] ................................................ A61B 8/06
[52] U.S. Cl. ............................ 128/661.09; 73/861.25
[58] Field of Search ...................... 128/661.01-661.10; 73/861.25

[56] References Cited

U.S. PATENT DOCUMENTS 4,803,990 2/1989 Bonnefous et al. .......... 73/861.25 X
4,928,698 5/1990 Bonnefous ................... 73/861.25 X

OTHER PUBLICATIONS

Electronic Letters; vol. 24, No. 4, Feb. 18, 1988, pp. 205-207; M. Nikoonahad et al.: "High-Resolution Ultrasound Transverse Flow Measurement".

*Primary Examiner*—Francis Jaworski
*Attorney, Agent, or Firm*—William Squire

[57] ABSTRACT

A device for measuring one of the transverse components $V_x$ of the speed of moving organs and blood flows by means of ultrasonic echography, the axial component $V_z$, oriented parallel to the axis $O_z$ of the ultrasonic beam, being measured by a first intercorrelation circuit (51$_z$) which operates with a sampling step $\Delta T$ and which supplies, on the basis of two successive echographic lines shifted through $k\Delta T$, $(k=-I, -I+1, \ldots, I)$, $2I+1$ correlation function values according to z, a first maximum-value searching circuit (53$_z$) which supplies the value $I_o$ of k which corresponds to the largest value of said correlation functions according to z. The device includes:

a bidimensional mosaic (10) of piezoelectric transducers which are centered around the origin O of a system of axes $O_x$, $O_y$ which forms a trihedron with said axis $O_z$, a circuit (20) for forming $2N_x+1$ receiving channels which correspond to the beams centered around $(k_xp_x,O,O)$, where $k_x=-N_x, -N_x+1, \ldots, N_x$ and $p_x$ is the pitch of the channels according to x, a buffer memory (50) in which there are stored the echographic signals received by each of the $2N_x+1$ receiving channels, taken for the values $I_o-1$, $I_o$, $I_o+1$ of k, a second circuit (51$_x$) for intercorrelation between a signal received by the central receiving channel (O,O,O) and the next signal received by the receiving channel $(k_xp_x, O,O)$ supplying the three intercorrelation functions $C_x(k_xp_x,O,(I_o-1)\Delta T)$, $c_x(k_xp_x,O,I_o\Delta T)$, $C_x(k_xp_x,O,(I_o+1)\Delta T)$, a circuit (53$_x$) for linear interpolation in x which supplies, on the basis of said 3 intercorrelation functions, the correlation peak $C_x(k_xp_x)$ according to x, a second maximum-value searching circuit (54$_x$), which supplies, on the basis of the $2N_x+1$ values of $k_x$, the value $k_{xo}$ for which $C_x(k_xp_x)$ is maximum, the tranverse component $V_x$ satisfying the equation:

$$V_x=k_{xo}p_x/T$$

where T is the recurrent period of the echographic signals.

Application: the formation of echographic images of moving organs and blood flows.

6 Claims, 3 Drawing Sheets

DIRECTIONAL COMPONENT MEASUREMENT BY ECHOGRAPHY

The invention relates to a device for measuring the speed of moving organs and blood flows by means of ultrasonic echography, the axial component Vz of the speed, oriented parallel to the axis $O_z$ of the ultrasonic scanning beam, being measured by means of on the the one hand a first intercorrelation circuit which operates with a samploing step $\Delta T$ and which supplies, on the basis of two successive echographic lines shifted through k $\Delta T$ (k=−I, −I'1, . . . I), 2I+1 correlation function values according to z, and on the other hand a first maximum searching circuit which supplies the value $I_o$ of k which corresponds to the largest value of said correlation functions according to z.

The invention is particularly advantageously used in the field of echographic examination of moving organs, for example cardiac walls, and blood flows in vessels.

Actually, the customarily used Doppler velocimeters only enable measurement of the axial speeds of the movements studied. This measurement can be carried out by different methods for processing the echographic signals, notably the intercorrelation method described in French Patent Application No. 2 590 790 corresponding to U.S. Pat. No. 4,803,990. This known method utilises the fact that the successive ultrasonic signals returned to the ultrasonic transducer by a moving target are related in accordance with the following equation:

$$S_{n+1}(t)=S_n(t=\tau_z)$$

$$\tau_z=2V_zT/C$$

where T is the recurrent period and C is the speed of sound.

The intercorrelation function between $S_n(t)$ and $S_{n+1}(t)$ is defined by:

$$\int S_{n+1}(t+u)S_n(d)dt=C_{nn}(u-\tau_z)$$

The function $C_{nn}$ $(u-\tau_z)$ is an autocorrelation function and, therefore, is maximum for $u=\tau_z$. Thus, a measurement of the time shift $96_z$, and hence of the axial speed $V_z$, can be performed by searching for which parameter u the intercorrelation function is maximum. To this end, the intercorrelation function is sampled, using a sampling step $\Delta T$, between $-I\ \Delta T$ and $+I\ \Delta T$ in steps of 1 so as to obtain 2I+1 correlation function values. The maximum value of the 2I+1 values corresponding to $u=Io\ \Delta T$, enables measurement of the axial speed $V_z$, utilising the equation:

$$V_z=IoC\Delta T/2T$$

French Patent Application No. 2 590 790 also teaches that, in order to eliminate errors which are inherent of the sampling during the determination of the maximum value of the correlation function, it is advantageous to use an interpolation circuit which supplies a more exact estimate of the axial speed on the basis of correlation function values.

However, this known measuring device does not provide any information whatsoever as regards the transverse components $V_x$ and $V_z$ of the speed of the movement or the flow studied. These two parameters, however, would be of major importance for determining, for example the blood flow rate and for achieving an improved imaging of blood flows.

The technical problem to be solved by the present invention is to realise a device for measuring, using ultrasonic echography, not only the axial component $V_z$ but also the transverse components $V_x$, $V_y$ of the speed of moving organs and blood flows.

A solution to this technical problem in accordance with the invention consists in that said device comprises:

a bidimensional mosaic of piezoelectric transducers which are centered around the origin 0 of a system of axes $O_x$, $O_y$ which form a trihedron with said axis $O_z$, a circuit for foming $2(N_x+N_y)+1$ receiving channels which correspond to the beams centered on the one hand around ($k_xp_x$, O,O), where $k_x=-N_x, -N_x+1, \ldots, N_x$ and $p_x$ is the pitch of the channels according to $x$, and on the other hand around (0 $k_yp_y$, O), where $k_y=N_y, -N_y, -N_y+1, \ldots, N_y$ and $p_y$ is the pitch of the channels according to y, a buffer memory in which there are stored the echographic signals received by each of the $2(N_x+N_y)+1$ receiving channels, taken for the values $I_o-1$, $I_o$, $I_o+1$ of k, a second and a third circuit for intercorrelation between a signal received by the central receiving channel (0,0,0) and the next signal received by the receiving channel ($k_xp_x$0,0) and (0, $k_yp_y$0), respectively, given the 3 intercorrelation functions $C_x(k_xp_x,0,(I_0-1)\Delta T$, $C_x(k_xp_x, 0I_0\Delta T)$, $C_x(k_xp_x,0,(I_0+1)\Delta T$, and $C_y(0, k_yp_y(I_0-1)\Delta T$, $C_y(0, k_yp_yI_0\Delta T$, $C_y(0, k_yp_y(I_0+1)\Delta T$, respectively, a circuit for linear interpolation in x and y, respectively, supplying the correlation peak $C_x(k_xp_x)$ according to x and $C_y(k_yp_y)$ according to y, respectively, on the basis of said 3 intercorrelation functions, a second and a third maximum-value searching circuit which supply, on the basis of the $2N_x+1$ values of $k_x$ and the $2N_y+1$ values of $k_y$, the values $k_{xo}$ and $k_{yo}$, respectively, for which $C_x(k_xp_x)$ and $C_y(k_yp_y)$, respectively, are maximum, the transverse components $V_x$ and $V_y$ satisfying the equations:

$$V_x=k_{xo}p_x/T$$

$$V_y=k_{yo}p_y/T$$

where T is the recurrent period of the echographic signals.

Assume that a scattering point having a speed V with components $V_x$, $V_y$ and $V_z$ is situated in the trihedron Oxyz at the point of the coordinates x, y, z, where z is the scanning depth. The $n^{th}$ echographic signal received by the channel centered around the point (0,0,0) of the mosaic is given by:

$$S_n(0,0,t)=\int\int p(x,y,t)D_n(x,y)dxdy$$

where p(x,y,t) is the diffraction response of the beam and $D_n(x,y)$ is the scatter response of the medium at the instant nT. $D_n(x,y)$ satisfies the following recurrence relation:

$$D_{n+1}(x,y)=D_n(x-V_xT,\ y-V_yT)$$

resulting in:

$$S_{n+1}(x,y,t)=S_n(x-V_xT,y-V_yT,t-2V_zT/C)$$

The intercorrelation function for the signals $S_n(0,0,t)$ and $S_{n+1}(0,0,t)$ is given by the expression:

$$C_{nn+1}(0,0,u) = \int S_n(0,0,t)S_{n+1}(0,0,t+u)dt = \int S_n(0,0,t)S_n(-V_xT,t-2V_zT/C+u)dt = C_{nn}(-V_xT,-V_yT,u-2V_zT/C)$$

With respect to the variable u, $C_{nn}$ is an autocorrelation function which assumes a maximum value for $u=2V_zT/C$. Thus, the same considerations underlying the above-mentioned method for measuring the axial speed $V_z$ are encountered, that is to say sampling on $2I+1$ samples with a step $\Delta T$ and searching the value $I_o$ which imparts the largest value to the intercorrelation function.

Let us consider $n^{th}$ echographic signal received on the channel centered around the point $(k_xp_x,0,0)$ of the mosaic:

$$S_n(k_xp_x,0,t)=\int\int p(x=k_xp_x,y,t)D_n(x,y)dt$$

The intercorrelation function for the signals $S_n(0,0t)$ and $S_{n+1}(k_x,p_x,0,t)$ is given by:

$$C_{nn+1}(k_xp_x,0,u) = \int S_n(0,0,t)S_{n+1}(k_xp_x,0,t+u)dt = \int S_n(0,0,t)S_n(k_xp_x-V_xT,-V_yT,t-2V_ZT/C+u)dt = C_{nn}(k_xp_x-V_xT,-v_yT,u-2V_ZT/C)$$

In order to enhance the measuring sensitivity, if desired, the intercorrelation function values between two consecutive signals n and n+1 can be accumulated in an accumulator.

$$C_x(k_xp_x,0,u)=\Sigma_xC_n(k_xp_x-V_xT,-V_yT,u-2V_ZT/C)$$

This correlation function in x is maximum for $u=2V_zT/C$.

Its maximum value $C_x(k_xp_x,0,2V_zT/C)$ is determined by linear interpolation on 3 values sampled with respect to u, taken around $I_o\,\Delta T$, to wit $(I_o-1)\Delta T$, $I_o\,\Delta T$, $(I_o+1)\,\Delta T$. The function $C_x(k_xp_x,0,2V_zT/C)=C_x(p_xk_x)$ is an autocorrelation function in x and is therefore maximum for $k_xp_x-V_xT=0$. By sampling on the $2N_{x+1}$ values of $k_x$ and searching for the maximum, that value $k_{xo}$ can be determined which produces the largest value of $C_x(k_xp_x)$.

Thus, the transverse speed according to x is equal to $$V_x=k_{xo}p_x/T$$

It can be demonstrated in the same way that the transverse speed according to y is given by:

$$V_y=k_{yo}p_x/T$$

where $k_{yo}$ corresponds to the maximum value of the intercorrelation function according to y $$C_y(p_yk_y) = C_y(0,k_yp_y,2V_zT/C) \text{ defined by}$$
$$C_y(0,k_yp_y,u) = \Sigma_nC_{nn}(-V_xT,k_yp_y-V_yT,u-2V_zT/C) = \Sigma_n\int S_n(0,0,t)S_{nn}(0,k_yp_y,t+u)dt$$

As for the axial speed $V_z$ a more exact estimate can be obtained for the transverse components $V_x$, $V_y$ which is no longer affected by errors caused by sampling. For this purpose, said second and third maximum-value searching circuits are followed by a first and a second interpolation circuit, respectively, which supplies the value $k_{xmax}$ and $k_{ymax}$, respectively, for which the intercorrelation function $C_x(k_xp_x)$ and $C_y(k_yp_y)$ respectively, is maximum, the transverse components satisfying the equations:

$$V_x=k_{xmax}p_x/T$$

$$V_y=k_{ymax}p_y/T$$

For ease of implementation, the first, the second and the third intercorrelation circuit are formed by 1-bit correlators in a sense that the signals $S_n$ and $S_{n+1}$ used are reduced to the sign of the ultrasonic signal. In this case the peak of the correlation function has the form of an isosceles triangle. It can also be arranged that the first and the second interpolation circuit perform a linear interpolation on the basis of the highest point and its two neighbors for complete reconstruction of the correlation peak, and hence for exact determination of the values of $k_{xmax}$ and $k_{ymax}$.

Finally, it is to be noted that for transverse speeds $V_{x,y}$ in the order of 50 cm/s and a recurrent frequency T of 200 μs, the quantity $V_{x,y}T$ amounts to approximately 0.1 mm. The pitch $p_x$ or $p_y$ between two consecutive beams should have an equivalent value. In practice the pitch between beams is approximately 0.3 mm in a practical linear array of transducers operating at 5 MHz. It is very well possible to realise an array with a pitch of 0.1 mm, but that would necessitate complex electronic circuitry for forming beams and would imply the use of high-impedance modules which are not compatible with the required low noise upon reception. In order to avoid this drawback, it is advantageous to connect a transverse interpolator so as to precede said buffer memory in order to reduce the pitches $p_x$ and $p_y$ by a factor n. In the above numerical example, the factor n equals 3. However, in the present description $p_x$ and $p_y$ are indiscriminately referred to as the real pitch or the fictitious pitch (divided by n) of the beams according to x and y.

Figure 2:
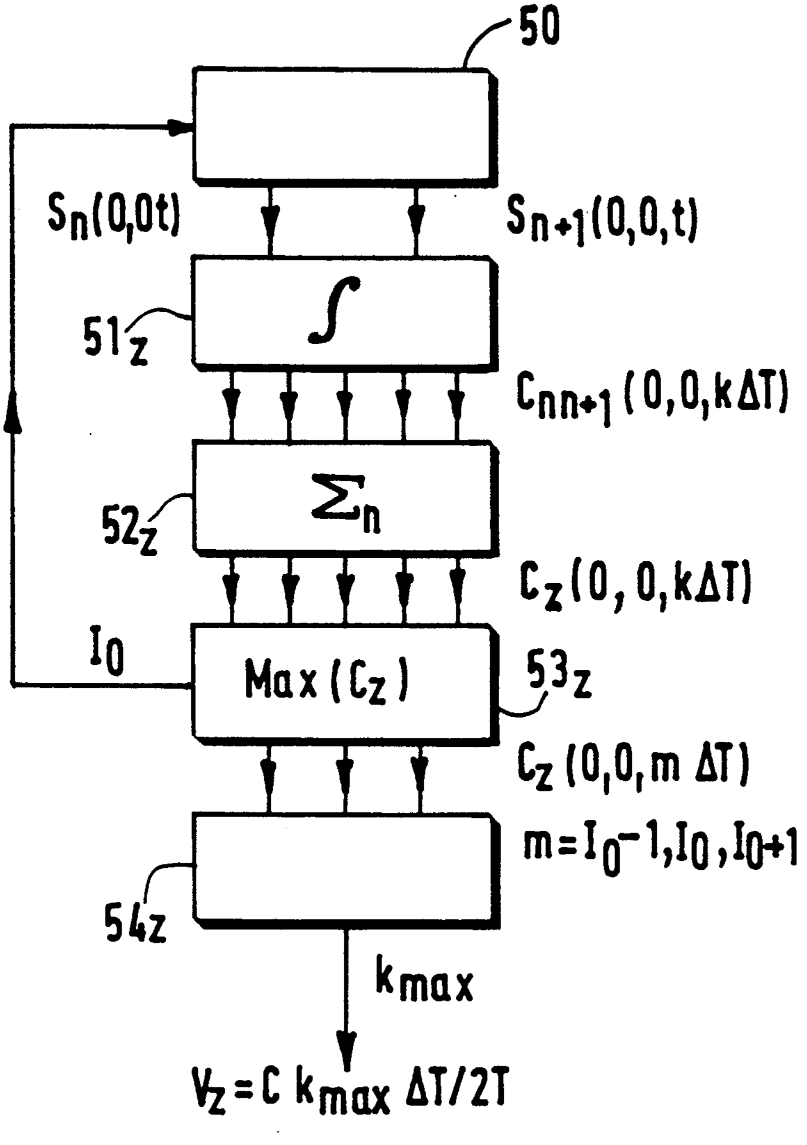
Figure 3:
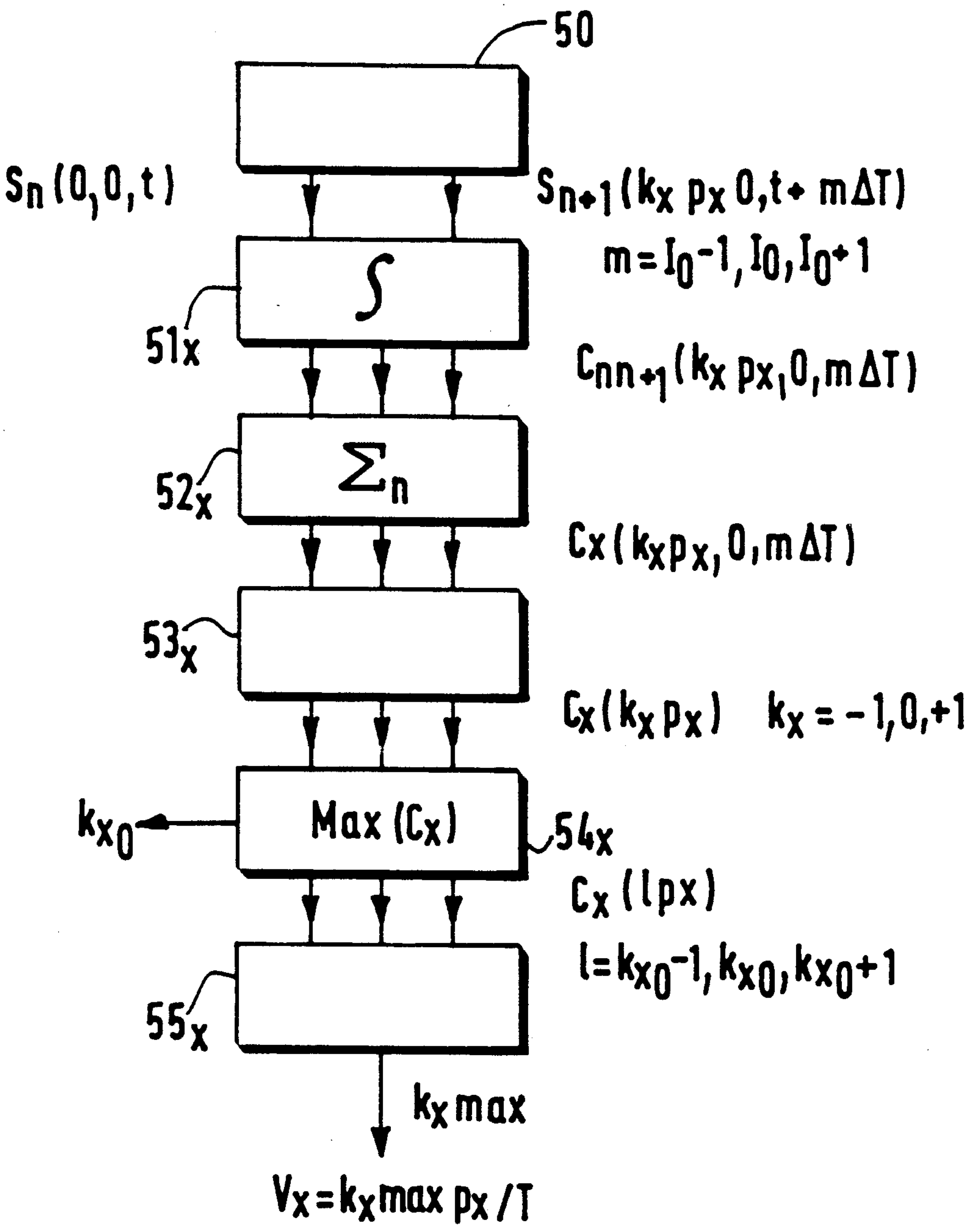

The invention will be described in detail hereinafter with reference to the accompanying diagrammatic drawings; therein:

FIG. 1 shows the block diagram of a device in accordance with the invention as far as the buffer memory, FIG. 2 shows the block diagram of the processing channel for the axial speed, and FIG. 3 shows the block diagram of the processing channel for the transverse speed.

FIG. 1 shows the block diagram of a device for measuring the components $V_x$, $V_y$ of the speed of moving organs and blood flows by means of ultrasonic echography. This device comprises a bidimensional mosaic 10 of piezoelectric transducers which is centered around the origin O of a system of axes $O_x$ and $O_y$ which form a trihedron with an axis z (not shown) perpendicular to the plane of the Figure, where $O_z$ defines the direction of the ultrasonic scanning beams. A circuit 20 for forming channels realizes $2(N_x'N_y)+1=5$ receiving channels (in this case $N_x=N_1=1$ is chosen), corresponding to beams centered in $(k_xp_x, 0,0)$, where $k_x=-1,0,1$, and in $(0, k_yp_y,0)$ where $k_y=-1,0,1$. The 5 beams thus defined are determined by the 5 zones of the mosaic 10 shown in FIG. 1. In the example shown, these zones have a square shape because in this case the pitches $p_x$ and $p_y$ are chosen to be equal. The 5 channels $e_n(k_xp_x, k_yp_y, t)$ are treated in a conventional manner by a circuit 30 for eliminating fixed echos. If necessary, a pitch reduction, for example by a factor 3, is established between the signals $e'_n(k_xp_x, k_yp_y, t)$ thus obtained by means of a linear interpolation device 40 which outputs the signals $e''_n$ given by $$e''_n(k_xp_x/3, k_yp_y/3, t) = 1/3e'_n(k_xp_x, k_yp_y, t) + 2/3e'_n(0,0,t) = S_n(k_xp_x, k_yp_y, t).$$

The signals $S_n(k_xp_x, k_yp_y, t)$ are then stored in a buffer memory 50.

FIG. 2 shows the processing channel which leads to the determination of the axial speed $V_z$. The signals $S_n(0,0,t)$ and $S_{n+1}(0,0,t)$, derived from the buffer memory 50 are correlated by the correlator $\mathbf{51}_z$, for example of the 1-bit type, and are sampled on 2I+1 sampling steps $\Delta T$. For each sample $k=-I, -I+1, \ldots, I$, the intercorrelation functions $C_{nn+1}(0,0, k\Delta T)$ are summed on n in an accumulator $\mathbf{52}_z$. Subsequently, a maximum-value searchign cicuit $\mathbf{53}_z$ supplies the value $I_o$ of the sample corresponding to the largest value of the correlation function $C_z(0,0, k\Delta T)$. This value $I_o$ is stored in the buffer memory 50 for later use during the measurement of the transverse speed. An approximate value of the axial speed $V_z$ is given by $V_z=CI_o\Delta T/2T$. In order to obtain a more exact value of $V_z$, a linear interpolation can be performed on the 3 values of the correlation function for $I_o-1$, $I_o$, $I_o+1$ in order to fine the absolute maximum value and the corresponding value of k, bine $k_{max}$, in $\mathbf{54}_z$ so that $V_z$ amounts to $Ck_{max}\Delta T/2T$.

FIG. 3 shows the block diagram of the processing channel which leads to the measurement of the component $V_x$ of the transverse speed, it being understood that an analogous treatment in y enables determination of the component $V_y$ in the same way.

On the basis of the signals $S_n(0,0t)$ and $S_{n+1}(k_xp_x,0, t+m\Delta T)$, where $m=I_o-1, I_o, I_o+1$, the (for example 1-bit) correlator $\mathbf{51}_x$ constructs the 3 correlation functions $C_{nn+1}(k_xp_xt+m\Delta T)$ which, once they have been summed by the accumulator $\mathbf{52}_x$, produce the intercorrelation functions $C_x(k_xp_x, t+m\Delta T)$. A linear interpolation circuit $\mathbf{53}_x$ subsequently calculates the correlation peak $C_x(k_xp_x)$ which corresponds to the maximum value of $C_x(k_xp_x,0, u)$ for u values between $(I_o-1)\Delta T$ and $(I_o+1)\Delta T$.

A maximum-value searching circuit $\mathbf{54}_x$ determines the value $k_{xo}$ of $k_x$ which offers the largest value of the correlation peak $C_x(k_xp_x)$; an appropriate value of the transverse speed $V_x$ is thus given by:

$$V_x=k_{xo}p_x/T$$

In order to obtain a higher precision for $V_x$, a linear interpolation is performed on the 3 values $C_x(k_{xo}=1)p_x)$, $C_x(k_op_x)$, $C_x((k_o+1)p_x)$ of the correlation peak in order to determine $k_{xmax}$ in $\mathbf{55}_x$ corresponding to the maximum value of the correlation peak, so that $V_x$ amounts to $$V_x=k_{xmax}p_x/T.$$

I claim:

1. An ultrasonic echographic system for measuring the speed components of moving organs and of blood flow with an ultrasonic scanning beam, comprising:

a first means which includes intercorrelation means for operating with a sampling step $\Delta T$ and which supplies, on the basis of two successive echographic lines shifted through $k\Delta T$ ($k=-I, -I+1, \ldots, I$) 2I+1 correlation function values according to z, and a first maximum-value searching means which supplies the value $I_o$ of k which corresponds to the largest value of said correlation functions according to z, for measuring the axial component $V_z$ of the speed, oriented parallel to the axis $0_z$ of the ultrasonic of the ultrasonic scanning beam; and means for the measurement of the transverse components $V_x$, $V_y$ of the speed, comprising:

a bidimensional mosaic of piezoelectric transducers which are centered around the origin O of a system of axes $O_x$, $O_y$ which forms a trihedron with said axis $O_z$;

means for forming $2(N_x+N_y)+1$ receiving channels which correspond to the beams centered around $(k_xp_x,0,0)$, where $k_x=-N_x, -N_x+1, \ldots, N_x$ and $p_x$ is the pitch of the channels according to x, and around $(0,k_yp_y,0)$, where $k_y=-N_y, -N_y+1 \ldots, N_y$ and $p_y$ is the pitch of the channels according to y;

a buffer memory means coupled to said channel forming means for storing the echographic signals received by each of the $2(N_x+N_y)+1$ receiving channels, taken for the values $I-_o-1$, $I_o$, $I_o+1$ of k;

second and third means coupled to said memory means for intercorrelation between a signal received by a central receiving channel (0,0,0) and the next signal received by the receiving channel $(k_xp_x,0,0)$ and $(0,k_yp_y,0)$, respectively, giving the intercorrelation functions $C_x(k_xp_x,0,(I_o-1)\Delta T)$, $C_x(k_xp_x,0,I_oT)$, $C_x(k_xp_x,0,(I_o+1)\Delta T)$ and $C_y(0,k_yp_y,(I_o-1)\Delta T)$, $C_y(0,k_yp_y,I_o\Delta T)$, $C_y(0,k_yp_y,(I_o+1)\Delta T$, respectively;

means for linear interpolation in x and y, respectively, supplying the correlation peaks $C_x(k_xp_x)$ according to x and $C_y(k_yp_y)$ according to y, respectively, on the basis of said intercorrelation functions; and second and third maximum-value searching means coupled to said interpolation means for supplying, on the basis of the $2N_x+1$ values of $k_x$ and the $2N_y+1$ values of $k_y$, the values $k_{xo}$ and $k_{yo}$, respectively, for which $C_x(k_xp_x)$ and $C_y(k_yp_y)$, respectively, are maximum, for determining transverse components $V_x$ and $V_y$ satisfying the equations:

$$V_x=k_{xo}p_x/T$$

$$V_y=k_{yo}p_y/T$$

where T is the recurrent period of the echographic signals.

2. A system as claimed in claim 1 wherein said second and third maximum-value searching means are followed by a first and a second interpolation means, respectively, for supplying the values $k_{xmax}$ and $k_{ymax}$, respectively, for which the intercorrelation functions $C_x(k_xp_x)$ and $C_y(k_yp_y)$, respectively, are maximum, for determining the transverse components satisfying the equations:

$$V_x=k_{xmax}p_x/T$$

$$V_yk_{ymax}p_y/T.$$

3. A system as claimed in claims 1 or 2, wherein the first, the second and the third intercorrelation means comprise 1-bit correlators.

4. A system as claimed in claim 3 wherein the first and the second interpolation means include means for performing a linear interpolation.

5. A system as claimed in claims 1 or 2 further comprising a transverse interpolating means which precedes said buffer memory means for reducing the pitches $p_x$ and $p_y$ by a factor n.

6. A system as claimed in claims 1 or 2 wherein the means for forming the channels is followed by means for eliminating fixed echos.

* * * * *